United States Patent [19]

Broemer et al.

[11] 4,365,356
[45] Dec. 28, 1982

[54] PROSTHESIS PARTS PROVIDED WITH A COATING OF A BIO-ACTIVE MATERIAL

[75] Inventors: Heinz Broemer; Werner Adam, both of Hermannstein; Friedhelm Hedrich, Edingen, all of Fed. Rep. of Germany

[73] Assignee: Ernst Leitz Wetzlar GmbH, Wetzlar, Fed. Rep. of Germany

[21] Appl. No.: 170,805

[22] Filed: Jul. 21, 1980

Related U.S. Application Data

[60] Continuation-in-part of Ser. No. 968,667, Dec. 12, 1978, abandoned, which is a division of Ser. No. 733,313, Oct. 18, 1976, Pat. No. 4,168,326.

[30] Foreign Application Priority Data

Oct. 18, 1975 [DE] Fed. Rep. of Germany ....... 2546824

[51] Int. Cl.$^3$ .............................................. A61F 1/24
[52] U.S. Cl. .......................................... 3/1.9; 3/1.91; 3/1.912; 128/92 C
[58] Field of Search ................ 3/1.91, 1.9, 1.912; 427/2; 128/92 C

[56] References Cited

U.S. PATENT DOCUMENTS

| 3,919,723 | 11/1975 | Heinke ................................. 3/1.9 |
| 3,919,723 | 11/1975 | Heinke et al. ....................... 3/1.9 |
| 3,922,155 | 11/1975 | Brimr .................................. 3/1.9 |
| 3,922,155 | 11/1975 | Broemer et al. ..................... 3/1.9 |
| 3,981,736 | 9/1976 | Broemer et al. ..................... 3/1.9 |
| 3,987,499 | 10/1976 | Scharbach et al. ................... 3/1.9 |
| 4,135,935 | 1/1979 | Pfeil ..................................... 3/1.9 |

FOREIGN PATENT DOCUMENTS

| 2340546 | 2/1972 | Fed. Rep. of Germany . |
| 2324867 | 11/1973 | Fed. Rep. of Germany . |
| 2326100 | 12/1974 | Fed. Rep. of Germany . |

OTHER PUBLICATIONS

Driskell et al., "Development of Ceramic and Ceramic Composite Devices for Maxillofacial Applications", J. Biomd. Mater, Res. Symp., No. 2, (part 2), pp. 345–361, (1962).
Hench, "Ceramic Implant", Resourc. Recovery, Proc. Ann. ASME Symp. 15th, 1975, pp. 197–205.

*Primary Examiner*—Sam Silverberg
*Attorney, Agent, or Firm*—Schwartz, Jeffery, Schwaab, Mack, Blumenthal & Koch

[57] ABSTRACT

Disclosed are novel prosthesis parts of improved properties which are obtained by providing a material as used for prosthesis with an enamel or enamel-like coating and incorporating in said enamel layer, while in a viscous state, a bio-active material. Such prosthesis parts have a satisfactory adhesive strength and coefficient of expansion, are substantially free of pores, are highly corrosion resistant, and readily grow intimately and firmly together with the bone tissue without the use of bone cement.

23 Claims, 3 Drawing Figures

PROSTHESIS PARTS PROVIDED WITH A COATING OF A BIO-ACTIVE MATERIAL

This application is a continuation-in-part of application Ser. No. 968,667, filed Dec. 12, 1978, now abandoned which is a divisional of application Ser. No. 733,313, filed Oct. 18, 1976, now U.S. Pat. No. 4,168,326, the disclosure of which is hereby incorporated by reference.

BACKGROUND OF THE INVENTION

1. Field of the Invention

The present invention relates to metallic prosthesis parts with layers of bio-active material, and to the use of such prosthesis parts for replacing animal and human bone.

2. Description of the Prior Art

Abnormal changes of and accidental injuries to bones and joints are remedied and eliminated at present by replacing the defective and damaged parts by prostheses made of inanimate materials which are foreign to the body, such as, for instance, metals, metal alloys, and plastic materials.

Recently, however, it has been found that metallic prosthesis parts which are anchored within the bone by means of plastic cements or adhesives, become loose after a certain period of time. Furthermore, frequently corrosion of the implanted materials has been observed. As a result thereof, for instance, hip-joint prosthesis are implanted, at present, almost exclusively in elderly patients only because implantation surgery in younger patients has to be repeated from time to time.

According to German Auslegeschrift (Application published for opposition) No. 23 06 552 corrosion can be avoided by selecting a suitable implant material or by coating the metallic prosthesis parts. However, even when proceeding in this manner, the prosthesis parts which are anchored within the bone still become loose. Thus, there is a need for a new implant material which adheres firmly to its implant bed without requiring anchoring by means of a bone cement.

It was believed that the oxidic ceramic materials ($Al_2O_3$) of high strength properties represent such materials. However, the assumption that such oxidic ceramic materials grow readily together with the live bone has not proved to be true. Although bones and tissue grow and adhere to the implant material and although bone substance is found also in the hollow spaces of the pores of an implant material having a porous surface, there has not been achieved a true complete union between bone and implanted prosthesis.

Although the oxidic ceramic materials possess no bio-activity, they represent an important raw material for producing implant parts. This is due to some of their properties such as, for instance, their high stability with respect to corrosive effects in the human organism and their high resistance to abrasion. This latter property represents an important parameter for the construction of moving parts of the body such as its joints. A joint implant which consists of a combination of metal or, respectively, metal alloy, which forms the shaft of the prosthesis, and of oxidic ceramic material which forms the ball and the socket of the joint has been disclosed in German Offenlegungsschrift (Published Application) No. 21 34 316. However, both said prosthesis parts are not bio-active and thus render it rather difficult to effect implantation without the use of a bone cement.

Recently new materials which enter into intimate and firm connection with living bone tissue on account of their chemical composition and structure have been developed. But these bio-active materials, for instance, bio-active glass ceramic material and bio-glass, do not have sufficiently high mechanical strength properties, so that it is not possible to produce therefrom load-carrying prosthesis parts. When coating the heretofore known implant materials with such bio-active agents, it is possible to firmly anchor the same in the bone tissue without the additional use of bone cement.

The objective is to provide a prosthesis which is both bio-active and possesses high load-carrying capacity, particularly for an indefinite period of time. With respect to the latter requirement, analyses of the movement and jumping action of the human body have shown that, under specific loads, pressure and stress peaks of seven times the body weight can occur. If it is desired to replace, for example, the femur by an endo-prosthesis, it is necessary based upon anatomical consideration for this replacement piece to conform essentially to the form, size and configuration of the natural skeleton portion being replaced. This means that the endo-prosthesis cannot be dimensioned cross-sectionally larger than its natural predecessor at the critical locations at which it is subjected to these enormous loads.

Practically speaking, in order to provide a prosthesis part having the required strength properties, it is necessary to employ a base member which is made of metal or a metal alloy. The basic problem to be solved, therefore, is the anchoring of the bio-active material to the base member. The layer of bio-active material must be permanently attached to the base member, so that it does not separate at any time after implantation in a patient's body.

Applying a layer of bio-active material to the prosthesis material according to known processes such as by spraying by the flame-spraying process or the plasma-spraying process, by dipping or by other methods, does not yield implant material of the required firmness of attachment and freedom from pores.

Furthermore, when the prosthesis material is coated in such a manner, there are encountered temperatures which, for instance, in the case of bio-active glass ceramic materials, partly destroy the crystallites which are responsible for growing together of the implant material and the bone tissue. To overcome this disadvantage, it was necessary to effect recrystallization of the glass ceramic material. For this purpose the coated implant part had again to be subjected to a heat treatment. However, temperatures of about 900 degrees C. as they are required to effect recrystallization, negatively affect the properties of metallic implant parts.

SUMMARY OF THE INVENTION

It is one object of the present invention to provide bio-active prosthesis parts regardless of which type of material is used for such parts, these parts being free of the disadvantages of the prior art prosthesis parts and having a satisfactory adhesive strength, being substantially free of pores, and not requiring high temperature treatment. These prosthesis parts possess novel and highly advantageous properties, especially of novel and advantageous surface properties.

Another object of the present invention is to provide prosthesis parts having surfaces of heretofore unknown quality and properties.

Another object of the present invention is to provide a method of using implant material as produced according to the novel process of this invention, for replacing bones and teeth and parts thereof in animals and humans.

In accomplishing the foregoing objects, there has been provided according to the present invention a prosthesis working piece comprising a structural metal or metal alloy core element; at least one carrier layer substantially free of pores applied to the core element, this carrier layer comprising an inorganic enamel which is compatible with the body; and a multitude of particles of bio-active material at least partly embedded in the carrier layer to provide a multitude of areas on which the bone tissue can grow together with the prosthesis. The bio-active material particles are partly embedded in the carrier layer by the steps of converting the carrier layer into a viscous state at a temperature which is not high enough to adversely affect the bio-active properties of the bio-active material and changing the structural properties of the core element, incorporating the bio-active material particles into the viscous carrier layer and thereafter causing the carrier layer to solidify.

Further objects, features and advantages of the invention will become apparent from the detailed description of preferred embodiments which follows, when considered together with the attached figures of drawing.

Other objects of the present invention and advantageous features thereof will become apparent as the description proceeds.

BRIEF DESCRIPTION OF THE DRAWINGS

Examples of prosthesis parts obtained according to the present invention are diagrammatically illustrated in the attached drawings, in which.

DETAILED DESCRIPTION OF PREFERRED EMBODIMENTS

Figure 1:
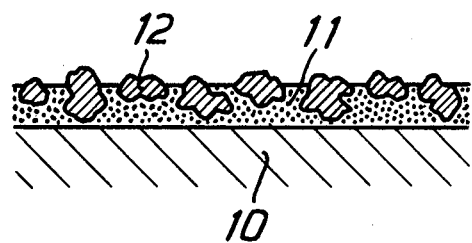
FIG. 1 is a cross-sectional view of a prosthesis part coated according to the present invention.

The process for producing prosthesis parts according to the present invention comprises the steps of (a) first providing the prosthesis part base with at least one enamel-like carrier layer compatible with the human or animal body, (b) causing the carrier layer to attain a viscous condition, (c) incorporating the bio-active material into the carrier layer while in such viscous condition, and (d) finally causing the thus bio-activated carrier layer to solidify.

According to a preferred embodiment of the present invention several enamel or enamel-like carrier layers of different composition and/or of different coefficient of expansion are applied to the prosthesis part. The bio-active materials can be applied to the carrier layer by spraying by means of air and/or gas under pressure. Or they can be pressed into the carrier layer by exerting mechanical pressure on the bio-active material dusted on or otherwise applied to the carrier layer.

Suitable bio-active materials are, for instance, glass ceramic materials and/or bio-glass. Preferred bio-active materials are those described, for instance, in U.S. Pat. No. 3,922,155.

The so-called bio-glass is a material described, for instance, by L. L. Hench and H. A. Paschall in "Direct Chemical Bond of Bio-Active Glass-Ceramic Materials to Bone and Muscle", published in *Journ. Biomed. Mater. Res. Symposium* No. 4, 1973, pages 25 to 42.

In addition thereto, or even exclusively, there can be used the starting materials for producing such glass ceramic materials and/or bio-glass.

Particularly preferred bio-active materials are bio-glass ceramic compositions developed in accordance with the present invention. These bio-glass ceramic compositions contain the following components:

Silicon dioxide ($SiO_2$): from about 42 to 48.5 weight %
Calcium metaphosphate ($Ca(PO_3)_2$): from about 12.5 to 18 weight %
Sodium oxide ($Na_2O$): from about 3.5 to 6 weight %
Potassium oxide ($K_2O$): from about 0 to 1.5 weight %
Magnesium oxide ($MgO$): from about 0 to 1.5 weight %
Calcium oxide ($CaO$): from about 28 to 35 weight %

One particularly preferred embodiment comprises

Silicon dioxide: 46 weight %
Calcium metaphosphate: 16 weight %
Sodium oxide: 5 weight %
Calcium oxide: 33 weight %

Preferably the bio-active coating materials are used in comminuted form. The particle size of the glass ceramic material may vary. Preferably the particle size is between about 50 $\mu$m and about 250 $\mu$m, and more preferably between about 80 $\mu$m and 180 $\mu$m.

Any known type of suitable prosthesis base material can be used. Although not limited thereto, the following materials are mentioned:

(1) Metals, for instance:
  Gold and/or platinum (see German Patent No. 583,589);
  Silver and/or tantalum (see German Patent No. 23 26 100);
  Titanium (see German Application Published For Opposition No. 21 38 881).
(2) Metal alloys, for instance:
  Aluminum alloys such as Duralumin (see German Published Application No. 23 59 826);
  Titanium alloys (see German Published Application No. 23 13 678);
  Cobalt-chromium-molybdenum alloys such as the alloy sold under the trademark Vitallium (see also German Published Application No. 23 13 678) by the firm Howmedico;
  Chromium-nickel-molybdenum alloys (see German Published Application No. 23 13 678);
  Cobalt-nickel-chromium alloys (see German Published Application No. 23 13 678).
Less preferred are the following:
(3) Oxidic ceramic materials, such as
  Sintered aluminum oxide (German Published Application No. 21 34 316);
  Zirconium dioxide and/or titanium dioxide (see German Published Application No. 23 18 459)
(4) Pyrolytic carbon, such as
  Graphite (see U.S. Pat. No. 3,526,005).

Of course, any known prosthesis material as used heretofore can be improved according to the present invention. Combinations of such materials, for instance, of a prosthesis core of metal and/or metal alloys and of a prosthesis casing or shell of oxidic ceramic material and/or pyrolytic carbon and others, can also be employed.

Reference is also made to the book on "Metallische Implantate in der Knochenchirurgie" [in translation: Metallic Implants in Bone Surgery] by E. Frank and H. Zitter, published by Springer, Vienna 1971.

Numerous enamel materials compatible with the human or animal body can be employed as the carrier material for the bio-active material. By the term "enamel" is meant conventional compositions, which are sometimes referred to as vitreous enamels or porcelain enamels and which are comprised of inorganic components, rather than the so-called enamel lacquers which frequently contain organic resins as the principal component. A history of enamelling and enamels may be found in Andrews, *Porcelain Enamels*, Garrard Press, 1961 or in *Vitreous Enamels* by Borax Consolidated, Ltd. 1960. The use of enamel coatings as primer layers for ceramic coatings on dental implants is discussed in Driskell et al, "Development of Ceramic and Ceramic Composite Devices for Maxillofacial Applications", *J. Biomed. Mater. Res. Symposium*, No. 2 (Part 2) pp. 345–361 (1972). Enamels as described in German Application Published for Opposition No. 12 91 597 have proved to be especially useful. See also the enamels as described in the publication "Emails" of the Borax Consolidated Ltd., London (1965) on enamels. Of course, lead oxide and other oxides or components which are harmful to the human or animal body should not be present in the carrier enamel layer. $B_2O_3$ and $Li_2O$ should be present not more than 5% by weight.

Preferred enamel compositions which have been developed in accordance with the present invention are those which fall within the several following definitions:

Definition I

Silicon dioxide ($SiO_2$): from about 50 to 65 weight %
Boron trioxide ($B_2O_3$): from about 0 to 12 weight %
Phosphorous pentoxide ($P_2O_5$): from about 0 to 3 weight %
Sodium oxide ($Na_2O$): from about 3 to 12 weight %
Potassium oxide ($K_2O$): from about 0 to 5 weight %
Calcium oxide (CaO): from about 0 to 3 weight %
Barium oxide (BaO): from about 0 to 1 weight %
Aluminum oxide ($Al_2O_3$): from about 2 to 7 weight %
Titanium dioxide ($TiO_2$): from about 6 to 14 weight %.

Definition II

Silicon dioxide ($SiO_2$): from about 35 to 45 weight %
Boron trioxide ($B_2O_3$): from about 4 to 8 weight %
Magnesium metaphosphate ($Mg(PO_3)_2$): from about 6 to 12 weight %
Lithium oxide ($Li_2O$): from about 1 to 5 weight %
Sodium oxide ($Na_2O$): from about 4 to 12 weight %
Magnesium oxide (MgO): from about 0 to 3 weight %
Calcium oxide (CaO): from about 12 to 20 weight %
Bismuth trioxide ($Bi_2O_3$): from about 1 to 5 weight %
Titanium dioxide ($TiO_2$): from about 4 to 12 weight %
Cryolite ($Na_3AlF_6$): from about 3 to 7 weight %.

Definition III

Silicon dioxide ($SiO_2$): from about 12 to 20 weight %
Boron trioxide ($B_2O_3$): from about 10 to 18 weight %
Phosphorous pentoxide ($P_2O_5$): from about 22 to 28 weight %
Lithium oxide ($Li_2O$): from about 2 to 6 weight %
Sodium oxide ($Na_2O$): from about 8 to 16 weight %
Potassium oxide ($K_2O$): from about 1 to 5 weight %
Magnesium oxide (MgO): from about 0 to 3 weight %
Aluminum oxide ($Al_2O_3$): from about 14 to 20 weight %
Titanium dioxide ($TiO_2$): from about 5 to 10 weight %
Cryolite ($Na_3AlF_6$): from about 0 to 2 weight %.

Definition IV

Silicon dioxide ($SiO_2$): from about 8 to 16 weight %
Boron trioxide ($B_2O_3$): from about 6 to 14 weight %
Magnesium metaphosphate ($Mg(PO_3)_2$): from about 7 to 15 weight %
Calcium metaphosphate: ($Ca(PO_3)_2$): from about 35 to 45 weight %
Lithium oxide ($Li_2O$): from about 3 to 6 weight %
Sodium oxide ($Na_2O$): from about 10 to 16 weight %
Potassium oxide ($K_2O$): from about 3 to 6 weight %
Titanium dioxide ($TiO_2$): from about 4 to 10 weight %.

Specific preferred enamel compositions are summarized in the following table:

| COMPONENT | COMPOSITION | | | | | |
|---|---|---|---|---|---|---|
| | A | B | C | D | E | F |
| Silicon dioxide ($SiO_2$) | 60 | 38 | 15.25 | 10.6 | 61.0 | 49.0 |
| Boron trioxide ($B_2O_3$) | 7.5 | 6 | 13.84 | 8.5 | 4.7 | 15.0 |
| Phosphorous pentoxide ($P_2O_5$) | 1.5 | — | 24.70 | — | — | — |
| Sodium oxide ($Na_2O$) | 9 | 10 | 13.18 | 13.5 | 16.7 | 14.5 |
| Potassium oxide ($K_2O$) | 3.5 | — | 2.99 | 4.5 | — | — |
| Calcium oxide (CaO) | 1 | 16 | — | — | — | — |
| Barium oxide (BaO) | 0.5 | — | — | — | — | — |
| Aluminum oxide ($Al_2O_3$) | 5 | — | 17.93 | — | — | — |
| Titanium dioxide ($TiO_2$) | 12 | 8 | 7.43 | 7.1 | 10.8 | 10.0 |
| Magnesium metaphosphate ($Mg(PO_3)_2$) | — | 10 | — | 9.8 | — | — |
| Lithium oxide ($Li_2O$) | — | 3 | 3.21 | 4.5 | 0.9 | 2.5 |
| Magnesium oxide (MgO) | — | 1 | 1.17 | — | 4.7 | 4.0 |
| Bismuth trioxide ($Bi_2O_3$) | — | 3 | — | — | — | — |
| Cryolite ($Na_3AlF_6$) | — | 5 | 0.30 | — | 1.2 | 5.0 |
| Calcium metaphosphate ($Ca(PO_3)_2$) | — | — | — | 41.5 | — | — |

The depth of penetration of the bio-active material into the carrier layer can be varied by varying the pressure employed for spraying the same onto the carrier layer and/or by varying the viscosity of the carrier layer. The carrier layer may be applied to the prosthesis part by processes known in enamelling technology. The bio-active material can be introduced into the carrier layer at the same time while the enamel carrier layer has not completely solidified.

It is also possible to apply the carrier layer to the prosthesis base part by means of the flame-spraying process or the plasma-spraying process and to introduce the bio-active material into the carrier layer at the same time while not yet solidified.

The carrier layer alone can also be applied to the prosthesis base part by the conventional processes as employed in enamel technology or by flame-spraying or by plasma-spraying. The prosthesis base part provided with the carrier layer is heated subsequently so as to convert the carrier layer into a fluid layer of the viscosity required for incorporating the bio-active material.

The required viscosity of the carrier layer can also be attained by heating the prosthesis base part with the enamel layer by means of a flame and/or by radiation, by placing both in a heating oven, by induction heating, or by passing the electric current directly therethrough.

The surface of the solidified carrier layer with the bio-active material incorporated thereinto can subsequently be ground and/or polished.

A prosthesis part produced according to the present invention is distinguished over heretofore known prosthesis parts by being provided with at least one enamel or enamel-like carrier layer which is compatible with the body and wherein the bio-active material is partly embedded. In a specific embodiment of the present invention the bio-active material particles protrude from the surface of the carrier layer, while in another embodiment the surface of the carrier layer with the bio-active material embedded therein is smoothly ground and/or polished.

As stated above, the prosthesis base part 10 as shown in FIG. 1 can be made of a suitable metal, of oxidic ceramic materials or of other materials. Its surface is cleaned and pretreated in a manner known per se so that a substantially clean surface is provided. The carrier layer 11 is then applied to the thus pretreated surface of the prosthesis base part by enamelling procedures as they are known to the art. The carrier layer consists of a non-toxic enamel or enamel-like material which is compatible with the body.

As mentioned hereinabove, one class of preferred enamel or enamel-like materials are those described in German Auslegeschrift No. 12 91 597, wherein it is disclosed in which manner its composition can be adjusted to any type of metallic base and to meet any desired requirements regarding corrosion resistance, adhesive strength, and coefficient of expansion. The composition of the enamel layer is not an object of the present invention.

As explained hereinabove, all the known processes of applying enamel compositions to a base, for instance, the wet process, the dry process, the electrophoretic process, the flame-spraying process, or the plasma-spraying process can be used for enamelling the prosthesis base parts. The carrier layer 11 may be applied as a single layer; but it may also be applied in several layers which may be of different composition and thus may have different coefficients of expansion.

The bio-active material 12 which, for instance, is in comminuted form, is incorporated into the carrier layer 11 while the layer is still in soft condition, for instance, by spraying it thereon by means of an air and/or gas blast.

The depth to which the individual particles of the bio-active material 12 penetrate into the enamel layer depends on the viscosity of the layer 11. Additionally, it can be varied by varying the pressure of the gas and/or air blast. The thickness of the bio-active layer is regulated by the amount of bio-active material 12 which is carried along by the air and/or gas blast. Said amounts of bio-active material can be varied so that they increase progressively from the interior of the carrier layer towards its surface by automatically regulating the air and/or gas blast and the amount of the bio-active material supplied.

Of course, the bio-active material 12 can be introduced into and/or upon the carrier layer by means of other processes, for instance, by pressing the bio-active material 12 into the enamelled layer by means of a mold fitting the prosthesis working piece.

It is understood that the bio-active material 12 need not be introduced into the carrier layer 11 according to the above described processes simultaneously with and/or directly subsequently to the application of said carrier layer 11. Working piece 10 can first be coated with the enamel carrier layer 11 and can be treated in a subsequent step of operation at any desired time so as to apply thereto the bio-active material 12.

In order to proceed in the last mentioned manner it is necessary that the prosthesis working piece 10 coated with a carrier layer 11 is subjected subsequently to such a heat treatment that a viscous state of a viscosity permitting incorporation of the bio-active material is imparted to the carrier layer 11.

Reheating of the enamel-coated working piece can be effected, for instance, by an open flame and/or heat radiation or by placing it in a heating oven, and, in the case of metallic prosthesis working pieces, by induction heating and/or by passing an electric current directly therethrough.

The advantages of the novel process according to the present invention are to be seen in the use of methods which are well known to the art and can be controlled readily in accordance with known manufacturing techniques.

In contrast to the known multi-layer coating process in which the individual layers are superposed and in which each layer per se forms a completely or almost completely self-contained layer, the bio-active material is incorporated according to the process of the present invention into the carrier layer in such a manner that the bio-active particles are partly embedded in the carrier layer and that they also adhere to the surface of said layer. As a result thereof the prosthesis working piece grows readily together with the body tissue even if the layer of bio-active material is not a completely continuous layer. Since the carrier layer covers the prosthesis working piece completely, the material for the prosthesis can be selected, for instance, solely according to the required strength.

The embodiment of the present invention as illustrated in FIG. 1 in which the enamel layer is coated with particles of bio-active material which partly protrude from the carrier layer has the advantage that a very large surface is formed and that, for instance, the bone tissue can readily grow onto said surface.

Figure 2:
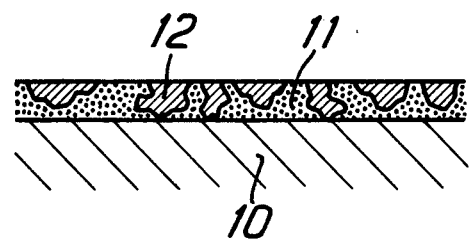
FIG. 2 is a cross-sectional view of such a prosthesis part with a polished surface.
Figure 3:
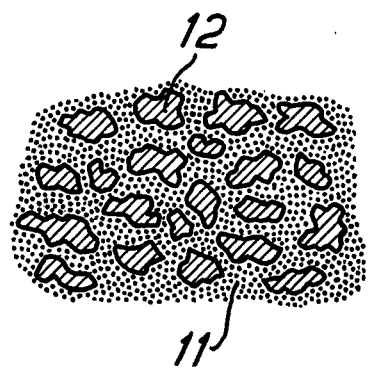
FIG. 3 is a top view of the surface illustrated in FIG. 2.

However, under certain conditions of use, it can be of advantage that the coated prosthesis working piece is provided with a smooth surface. In this case the surface of bio-active material coated prosthesis parts can be ground and/or polished as this is illustrated in FIG. 2. The smooth surface of such a coated prosthesis working piece is provided, depending on the density of the bio-active material particles incorporated into the enamel layer, with a multitude of elementary areas of bio-active material on which growing together of the prosthesis with the body tissue can take place. FIG. 3 illustrates the smooth surface in which the bio-active particles are shown.

The following examples serve to illustrate the present invention and more particularly suitable compositions of the prosthesis, the enamel layer, and the bio-active material without, however, limiting the same thereto.

EXAMPLE 1

A hip-thigh joint prosthesis according to the present invention is produced by first enamelling suitably shaped pieces of a cobalt-chromium-molybdenum alloy by any of the known enamelling methods with the following enamel composition, in parts by weight:

Silicon dioxide ($SiO_2$) 61.0 weight %
Boron trioxide ($B_2O_3$) 4.7 weight %
Lithium oxide ($Li_2O$) 0.9 weight %
Sodium oxide ($Na_2O$) 16.7 weight %
Magnesium oxide (MgO) 4.7 weight %
Titanium dioxide ($TiO_2$) 10.8 weight %
Cryolite ($Na_3AlF_6$) 1.2 weight %

After providing the prosthesis core part with an enamel layer of about 0.3 mm thickness, the resulting enamelled prosthesis is heated to a temperature of about 680° C., whereby the enamel layer becomes of softened viscous consistency.

A bio-active material of the following composition, in weight %, is finely comminuted to a particle size between about 100 μm and about 175 μm:

| COMPONENT | a | b | c | d | e | f | g |
|---|---|---|---|---|---|---|---|
| $SiO_2$ | 46.2 | 43.0 | 43.0 | 43.0 | 46.0 | 45.0 | 43.0 |
| $Ca_3(PO_4)_2$ | 25.5 | 21.0 | 21.0 | 21.0 | — | — | 21.0 |
| $Ca(PO_3)_2$ | — | — | — | — | 13.4 | 13.9 | — |
| CaO | 20.2 | 15.0 | 11.8 | 11.0 | 18.6 | 1.1 | 10.0 |
| MgO | 2.9 | 8.0 | 11.5 | 11.5 | 11.5 | 30.0 | 10.5 |
| $Na_2O$ | 4.8 | 12.0 | 5.9 | 5.7 | 5.7 | 5.0 | 5.7 |
| $K_2O$ | 0.4 | 1.0 | 6.8 | 6.8 | 3.8 | 5.0 | 6.8 |
| $CaF_2$ | — | — | — | 1.0 | 1.0 | — | 3.0 |

The particles of bio-active material are then sprayed upon the softened, viscous enamel layer of the prosthesis so that they penetrate into said layer and are incorporated thereinto. The particles protrude to a certain extent from the surface of the prosthesis as shown in FIG. 1. After cooling and solidifying the enamel layer the resultant prosthesis is finely ground and polished to yield a smooth surface as shown in FIGS. 2 and 3.

The resulting prosthesis is implanted surgically into the patient and readily grows into the hip and other bone tissue. Such prosthesis have proved to replace joints which are diseased or which are painful, such as the hip joint, the elbow joint, the shoulder joint, or finger joints. For instance, the head, neck, and part of the shaft of the femur may be replaced by arthroplasty by the correspondingly shaped prosthesis parts according to the present invention. The crushed lower part of humerus, i.e., the upper bone in the elbow or the upper part of the humerus connecting to the shoulder have also been surgically replaced successfully by correspondingly shaped prosthesis parts according to the present invention.

Of course, many changes and variations in the composition of the bio-active material, the enamel carrier layer, and the prosthesis core material, in the manner in which the prosthesis core material is enamelled and the bio-active material is incorporated into the enamel carrier layer, and the like may be made by those skilled in the art in accordance with the principles set forth herein and in the claims annexed hereto.

What is claimed is:

1. A prosthesis working piece comprising: a structural core element; at least one carrier layer substantially free of pores applied to said core element, said carrier layer comprising an inorganic enamel which is compatible with the body; and a multitude of particles of a bio-active material at least partly embedded in said carrier layer to provide a multitude of exposed areas of the particles on which the bone tissue can grow together with the prosthesis, said bio-active material particles having a particle size of at least about 50 μm.

2. A prosthesis working piece according to claim 1, wherein said bio-active material particles protrude from the surface of said carrier layer.

3. A prosthesis working piece according to claim 1, wherein the surfaces of said bio-active material particles are flush with the surface of said carrier layer.

4. A prosthesis working piece according to claim 1, wherein said bio-active material particles have a particle size between about 50 μm and 250 μm.

5. A prosthesis working piece according to claim 4, wherein said bio-active material particles have a particle size between about 80 μm and 180 μm.

6. A prosthesis working piece according to claim 1, wherein said bio-active material comprises a bio-glass ceramic composition.

7. A prosthesis working piece according to claim 1, wherein said inorganic enamel composition comprises
Silicon dioxide ($SiO_2$) from about 50 to 65 weight %
Boron trioxide ($B_2O_3$) from about 0 to 12 weight %
Phosphorous pentoxide ($P_2O_5$) from about 0 to 3 weight %
Sodium oxide ($Na_2O$) from about 3 to 12 weight %
Potassium oxide ($K_2O$) from about 0 to 5 weight %
Calcium oxide (CaO) from about 0 to 3 weight %
Barium oxide (BaO) from about 0 to 1 weight %
Aluminum oxide ($Al_2O_3$) from about 2 to 7 weight %
Titanium dioxide ($TiO_2$) from about 6 to 14 weight %.

8. A prosthesis working piece according to claim 7, wherein said inorganic enamel composition comprises
Silicon dioxide ($SiO_2$)—60.0 weight %
Boron trioxide ($B_2O_3$)—7.5 weight %
Phosphorous pentoxide ($P_2O_5$)—1.5 weight %
Sodium oxide ($Na_2O$)—9.0 weight %
Potassium oxide ($K_2O$)—3.5 weight %
Calcium oxide (CaO)—1.0 weight %
Barium oxide (BaO)—0.5 weight %
Aluminum oxide ($Al_2O_3$)—5.0 weight %
Titanium dioxide ($TiO_2$)—12.0 weight %.

9. A prosthesis working piece according to claim 1, wherein said inorganic enamel composition comprises
Silicon dioxide ($SiO_2$) from about 35 to 45 weight %
Boron trioxide ($B_2O_3$) from about 4 to 8 weight %
Magnesium metaphosphate ($Mg(PO_3)_2$) from about 6 to 12 weight %
Lithium oxide ($Li_2O$) from about 1 to 5 weight %
Sodium oxide ($Na_2O$) from about 4 to 12 weight %
Magnesium oxide (MgO) from about 0 to 3 weight %
Calcium oxide (CaO) from about 12 to 20 weight %
Bismuth trioxide ($Bi_2O_3$) from about 1 to 5 weight %
Titanium dioxide ($TiO_2$) from about 4 to 12 weight %
Cryolite ($Na_3AlF_6$) from about 3 to 7 weight %.

10. A prosthesis working piece according to claim 9, wherein said inorganic enamel composition comprises
Silicon dioxide ($SiO_2$)—38 weight %
Boron trioxide ($B_2O_3$)—6 weight %
Magnesium metaphosphate ($Mg(PO_3)_2$)—10 weight %
Lithium oxide ($Li_2O$)—3 weight %
Sodium oxide ($Na_2O$)—10 weight %
Magnesium oxide (MgO)—1 weight %
Calcium oxide (CaO)—16 weight %
Bismuth trioxide ($Bi_2O_3$)—3 weight %
Titanium dioxide ($TiO_2$)—8 weight %
Cryolite ($Na_3AlF_6$)—5 weight %.

11. A prosthesis working piece according to claim 1, wherein said inorganic enamel composition comprises
Silicon dioxide ($SiO_2$) from about 12 to 20 weight %
Boron trioxide ($B_2O_3$) from about 10 to 18 weight %

Phosphorous pentoxide ($P_2O_5$) from about 22 to 28 weight %
Lithium oxide ($Li_2O$) from about 2 to 6 weight %
Sodium oxide ($Na_2O$) from about 8 to 16 weight %
Potassium oxide ($K_2O$) from about 1 to 5 weight %
Magnesium oxide (MgO) from about 0 to 3 weight %
Aluminum oxide ($Al_2O_3$) from about 14 to 20 weight %
Titanium dioxide ($TiO_2$) from about 5 to 10 weight %
Cryolite ($Na_3AlF_6$) from about 0 to 2 weight %.

12. A prosthesis working piece according to claim 11, wherein said inorganic enamel composition comprises
Silicon dioxide ($SiO_2$)—15.25 weight %
Boron trioxide ($B_2O_3$)—13.84 weight %
Phosphorous pentoxide ($P_2O_5$)—24.70 weight %
Lithium oxide ($Li_2O$)—3.21 weight %
Sodium oxide ($Na_2O$)—13.18 weight %
Potassium oxide ($K_2O$)—2.99 weight %
Magnesium oxide (MgO)—1.17 weight %
Aluminum oxide ($Al_2O_3$)—17.93 weight %
Titanium dioxide ($TiO_2$)—7.43 weight %
Cryolite ($Na_3AlF_6$)—0.30 weight %.

13. A prosthesis working piece according to claim 1, wherein said inorganic enamel composition comprises
Silicon dioxide ($SiO_2$) from about 8 to 16 weight %
Boron trioxide ($B_2O_3$) from about 6 to 14 weight %
Magnesium metaphosphate ($Mg(PO_3)_2$) from about 7 to 15 weight %
Calcium metaphosphate ($Ca(PO_3)_2$) from about 35 to 45 weight %
Lithium oxide ($Li_2O$) from about 3 to 6 weight %
Sodium oxide ($Na_2O$) from about 10 to 16 weight %
Potassium oxide ($K_2O$) from about 3 to 6 weight %
Titanium dioxide ($TiO_2$) from about 4 to 10 weight %.

14. A prosthesis working piece according to claim 13, wherein said inorganic enamel composition comprises
Silicon dioxide ($SiO_2$)—10.6 weight %
Boron trioxide ($B_2O_3$)—8.5 weight %
Magnesium metaphosphate ($Mg(PO_3)_2$)—9.8 weight %
Calcium metaphosphate ($Ca(PO_3)_2$)—41.5 weight %
Lithium oxide ($Li_2O$)—4.5 weight %
Sodium oxide ($Na_2O$)—13.5 weight %
Potassium oxide ($K_2O$)—4.5 weight %
Titanium dioxide ($TiO_2$)—7.1 weight %.

15. A prosthesis working piece according to claim 6, wherein said bio-glass ceramic composition comprises
Silicon dioxide ($SiO_2$) from about 42 to 48.5 weight %
Calcium metaphosphate ($Ca(PO_3)_2$) from about 12.5 to 18 weight %
Sodium oxide ($Na_2O$) from about 3.5 to 6 weight %
Potassium oxide ($K_2O$) from about 0 to 1.5 weight %
Magnesium oxide (MgO) from about 0 to 1.5 weight %
Calcium oxide (CaO) from about 28 to 35 weight %.

16. A prosthesis working piece according to claim 15, wherein said bio-glass ceramic composition comprises
Silicon dioxide ($SiO_2$)—46 weight %
Sodium oxide ($Na_2O$)—5 weight %
Calcium oxide (CaO)—33 weight %
Calcium metaphosphate ($Ca(PO_3)_2$)—16 weight %.

17. A prosthesis working piece according to claim 1, wherein said inorganic enamel composition comprises
Silicon dioxide ($SiO_2$)—61.0 weight %
Boron trioxide ($B_2O_3$)—4.7 weight %
Sodium oxide ($Na_2O$)—16.7 weight %
Titanium dioxide ($TiO_2$)—10.8 weight %
Lithium oxide ($Li_2O$)—0.9 weight %
Magnesium oxide (MgO)—4.7 weight %
Cryolite ($Na_3AlF_6$)—1.2 weight %.

18. A prosthesis working piece according to claim 1, wherein said inorganic enamel composition comprises
Silicon dioxide ($SiO_2$)—49.0 weight %
Boron trioxide ($B_2O_3$)—15.0 weight %
Sodium oxide ($Na_2O$)—14.5 weight %
Titanium dioxide ($TiO_2$)—10.0 weight %
Lithium oxide ($Li_2O$)—2.5 weight %
Magnesium oxide (MgO)—4.0 weight %
Cryolite ($Na_3AlF_6$)—5.0 weight %.

19. A prosthesis working piece according to claim 1, wherein said bio-active material comprises a bio-glass composition or a bio-glass ceramic composition.

20. A prosthesis working piece according to claim 1, wherein said structural core element comprises a metal or metal alloy.

21. A prosthesis working piece according to claim 1, wherein said bio-active material particles are partly embedded in said carrier layer by the steps of converting said carrier layer into a viscous state at a temperature which is not high enough to adversely affect the bio-active properties of said bio-active material or change the structural properties of the core element, incorporating said bio-active material particles into the viscous carrier layer and thereafter causing the carrier layer to solidify.

22. A prosthesis working piece according to claim 1, comprising a plurality of inorganic enamel carrier layers.

23. A prosthesis working piece according to claim 22, wherein at least two of said inorganic enamel carrier layers have a different coefficient of thermal expansion.

* * * * *